United States Patent [19]

Gauntley et al.

[11] 4,159,193

[45] Jun. 26, 1979

[54] METHOD FOR SAMPLING AND FIXING URINARY METABOLITES ON AN IMMOBILIZING SUPPORT AND APPARATUS THEREFOR

[75] Inventors: Philippe Gauntley, Tomblaine; Jean-Louis Magadur, Cuinzier; Georges Morel, Dombasle, all of France

[73] Assignee: I.N.R.S., Institut National de Recherche et de Securite pour la Prevention des Accidents du travail et des Maladies Professionnelles, Paris, France

[21] Appl. No.: 791,330

[22] Filed: Apr. 27, 1977

[30] Foreign Application Priority Data

Apr. 29, 1976 [FR] France .................. 76 12788
Mar. 29, 1977 [FR] France .................. 77 09364

[51] Int. Cl.² ............... G01N 33/16; G01N 21/06; G01N 31/06; G01N 31/22
[52] U.S. Cl. .................. 23/230 B; 252/408; 422/55; 422/58; 422/101; 422/102
[58] Field of Search .................. 23/253 TP, 259, 292, 23/230 B; 422/55, 58, 101, 102

[56] References Cited

U.S. PATENT DOCUMENTS

| | | | |
|---|---|---|---|
| 3,642,450 | 2/1972 | Eriksson | 23/253 TP |
| 3,645,692 | 2/1972 | Stork | 23/230 B |
| 3,741,727 | 6/1973 | Stroterhoff | 23/253 TP |
| 3,849,256 | 11/1974 | Linder | 23/253 TP |
| 3,954,412 | 5/1976 | Ogdwa | 23/253 TP |
| 4,066,646 | 1/1978 | LeBlanc | 422/102 |
| 4,073,693 | 2/1978 | Janin | 422/102 |

OTHER PUBLICATIONS

L. H. del Portal, Clin. Chim. Acta, 34, 487–488 (1971).
Chemical Abstracts, 83:157644z (1975).
Chemical Abstracts, 75:148422h (1971).
Chemical Abstracts, 85:59070f (1976).
V. P. Dole, JAMA, 198 (4), pp. 115–118 (1966).

*Primary Examiner*—Sidney Marantz

[57] ABSTRACT

A method for sampling and fixing urinary metabolites on an immobilizing support which is a paper comprising a substance appropriately activated before use. The determination of the or each required metabolite is expressed in relation to the determination of a metabolite where excretion is constant with time. The appropriately activated substance may be an ion exchange resin or silica gel. The method may be used for determining delta-aminolevulinic acid (ALA), or trichloroacetic acid and trichloroethanol conjugated with glucuronic acid, in urine samples.

26 Claims, 6 Drawing Figures

METHOD FOR SAMPLING AND FIXING URINARY METABOLITES ON AN IMMOBILIZING SUPPORT AND APPARATUS THEREFOR

BACKGROUND OF THE INVENTION

The present invention relates to a method for sampling and fixing urinary metabolites on an immobilizing support and apparatus therefor.

The present invention enables certain medical analyses to be carried out on large population groups under satisfactory conditions.

It is well known that mass medical examinations, e.g. in a factory when checking on occupational diseases, encounter numerous difficulties, such as carrying out the biological sampling, particularly of urine, storing the samples, transporting the samples to the laboratory where the relatively complex analyses can be carried out and the mass arrival of these samples at the laboratory, which cannot process all the samples immediately so that some of them must be left waiting.

PRIOR ART

To overcome these disadvantages, and in the particular case of the determination of delta-aminolevulinic acid, a characteristic metabolite of lead poisoning, Lester Hankin and Associates (Clinical Pediatrics, December 1970, Volume 9, No. 13, pages 707 to 712) have proposed that the urine samples should not be transported to the laboratory but that instead the urinary metabolites should be absorbed at the actual collecting site, on a piece of paper impregnated with a cation exchanger resin (No SA 2, sulphonic acid resin in the $Na^+$ form), by briefly dipping the paper into the urine, allowing it to dry, packing it suitably and sending it to the laboratory by post. On receipt of the piece of paper, the laboratory desorbs the metabolites fixed on the cation exchanger resin by subjecting it to the action of an acetate buffer and carries out the colorimetric reaction which enables the determination to be made.

This reaction comprises forming a pyrrole by reacting delta-aminolevulinic acid (ALA) with acetyl acetone, and then reacting the pyrrole with Ehrlich's reagent, to give a coloured complex which can be determined by colorimetry. A calibration curve prepared from a urea solution is used for the reading.

As far as Applicants are aware, this prior art process has not been used on a large scale and this may be due to the fact that the colorimetric reaction used for the determination is not specific to the pyrrole formed in the reaction between ALA and acetyl acetone. It is influenced by numerous factors, more particularly the possible presence of Ehrlich positive and Ehrlich negative compounds, urea, etc. in the urine.

Although the Hankin process allows for the presence of urea by proposing that the readings should be taken on a calibration curve from a urea solution, it does not allow for the unwanted metabolites comprising the Ehrlich positive and Ehrlich negative compounds. The essential improvement to be made to the Hankin process is therefore, primarily, to eliminate these unwanted metabolites which falsify the determination and the simplest solution would appear to be carefully to wash the resin-impregnated paper before desorption of the ALA.

Unfortunately, the paper SA 2 in the $Na^+$ form used by Hankin does not fix the ALA sufficiently to allow such washing since the washing results in a loss of ALA which may be as much as 51% and which, furthermore, is not even constant.

It is an object of the present invention to overcome this disadvantage by proposing an immobilizing support, the properties of which are such as to guarantee that the wanted metabolites are sufficiently fixed so that the elimination of the unwanted metabolites entails only a small and constant loss of the wanted metabolites.

SUMMARY OF THE INVENTION

The present invention provides a method for sampling and fixing urinary metabolites on an immobilizing support which is readily transportable to an analysis centre for determining, at least one of the metabolites, which comprises the steps of:
  (i) contacting the support with the urine so as to sample a specimen thereof and to fix urinary metabolites on the support;
  (ii) transporting the support to an analysis centre;
  (iii) removing from the support unwanted metabolites which are likely to distrub the determination of the or each required metabolite; and
  (iv) eluting and determining the or each required metabolite;
the improvement comprising using as the support a paper comprising a substance appropriately activated before use and expressing the determination of the or each required metabolite in relation to the determination of a metabolite whose excretion is constant with time.

DESCRIPTION OF THE PREFERRED EMBODIMENTS

More specifically, in carrying out the method of the invention, the support used is preferably a paper comprising a material which is suitably activated before use.

The paper treated with the suitably activated material itself forms the sampling means and it will be understood that the amount of the sample depends on the quality of the paper and that for a paper of constant quality the amount of urine sampled can be known with good accuracy.

Nevertheless, to avoid the results being falsified by variations in the level of the amount of urine sampled or, in particular, by variations in the dilution of the urine which varies greatly according to the time at which the sampling is made and the amount of liquid intake, etc. the result of the determination of the or each wanted metabolite is expressed, in the method of the invention, relative to the result of the determination of a metabolite whose excretion is constant per unit of time.

In a first embodiment of the invention, the suitably activated material comprised by the paper is an ion-exchange resin.

The resins suitable for carrying out the method of the invention are selected, for example, from those whose properties are given in the following Table I, although it is to be understood that this list is not limiting.

TABLE I

| Skeleton | Functional group | Functional type |
|---|---|---|
| Polystyrene | $ArSO_3H$ | strong acid |
| Aliphatic polymer | —COOH | weak acid |
| Polystyrene | $—N(CH_3)_2$ | strong base |
| Copolymer | Polyamine | weak base |

Taking the specific case of the polystyrene skeleton resin with a functional group $ArSO_3H$ (which corresponds to the form $Na^+$ resin used to impregnate the No SA 2 paper used by Hankin), activation comprises transferring it to a more acid form chosen between $NH_4^+$, $Li^+$ and $H^+$. To achieve this result, the ion-exchange resin is contacted with a compound adapted to provide it with the required ion, such as $NH_4OH$, LiCl or HCl.

In the activated $H^+$ form, the polystyrene skeleton resin of functional group $ArSO_3H$ fixes ALA much better than in the original $Na^+$ form. This is apparent from the tests shown in Table II below, in which strips of No SA 2 paper, $H^+$ activated and $Na^+$ non-activated, were impregnated with 100 μl of a 40 mg/l ALA solution with an addition of 1.6 mg/l of highly radioactive ALA (125600 disintegrations per minute), and the impregnated strips were washed twice.

TABLE II

| | ALA fixed | Loss on first wash | Loss on second wash | Total loss |
|---|---|---|---|---|
| $H^{30}$ | 169 ± 9.3 | 1 ± 0.1 | 0.37 ± 0.02 | 1.38 ± 0.08 |
| $Na^{30}$ | 115 ± 9.2 | 29 ± 3 | 16 ± 1.4 | 45 ± 4.3 |

Tests have shown that for carrying out the method of the invention for determining the ALA it is preferable to activate the polystyrene skeleton resin of the functional group $ArSO_3H$ so that it is in the $H^+$ form rather than in another activated form, and the results set out in Table III show that the $NH_4^+$ and $Li^+$ forms retain less ALA than the non-activated $Na^+$ form.

TABLE III

| Strips of paper impregnated with polystyrene $ArSO_3H$ resin | Activated forms | | | Non-activated form |
|---|---|---|---|---|
| | $NH_4^+$ | $Li^+$ | $H^+$ | $Na^+$ |
| Quantity fixed | 100% | 100% | 100% | 100% |
| Loss on 1st wash | 83% ± 10 | 76% ± 11 | 1% ± 0.1 | 30% ± 4 |
| Loss on 2nd wash | 12% ± 2 | 15% ± 2 | 0.4 ± 0.04 | 21% ± 3 |
| Recovered from the eluate | 5% ± 0.6 | 9% ± 2 | 98% ± 11 | 49% ± 5 |

The unwanted metabolites fixed on the activated resin are eliminated by repeated washing in water with agitation (for example twice for 10 minutes), whereupon the resin is dried.

The ALA is then desorbed by bringing the resin into contact with an acid buffer and the ALA is determined by the general use of the coloured reaction obtained with Ehrlich's reagent under the conditions set out hereinbefore.

Various urinary ALA determination techniques have also been previously proposed. They are techniques related to those of Mauzerall and Granick and to that of Grabecki.

A—Mauzerall and Granick related techniques

Figure 1:
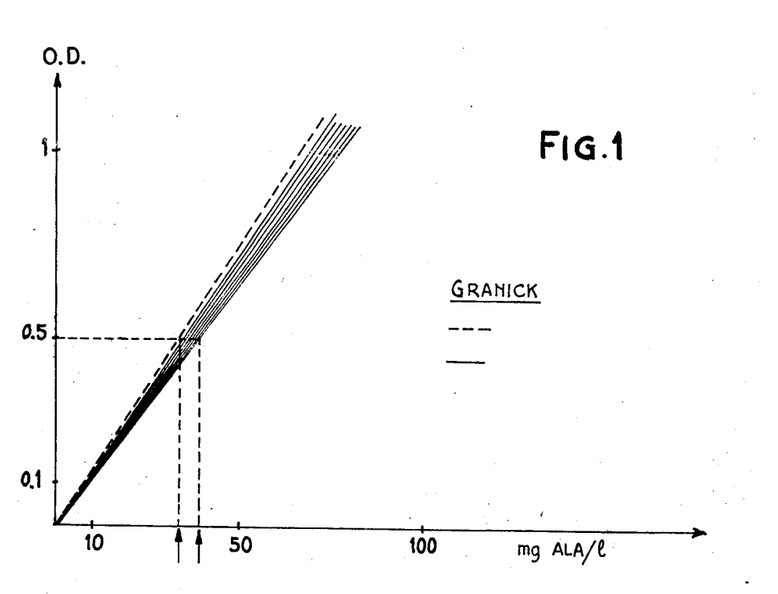
FIG. 1 is a graph of ALA scales produced from the results of measurement on ten urine samples using Mauzerall and Granick's technique.

Urine samples are passed through two ion-exchange columns, one an anion and the other a cation exchange column, so that the endogonous pyrroles and Ehrlich positive substances are eliminated, the urea is eliminated and certain Ehrlich negative substances which have an interfering action are removed. The final dilution is 1/28. A standard reading curve is prepared in water without passage through the resins. ALA scales produced by this technique from 10 urine samples give a dispersion of the results as shown in FIG. 1 of the accompanying drawings. The fact that the standard curve prepared in water is used results in some uncertainty due to systematic default and this may be as much as −38% of the true value.

B—Grabecki related techniques

These techniques are characterised by the fact that the Ehrlich negative substances are not extracted. The contribution of the Ehrlich positive substances is deduced by measuring a "blank urine". The final value is 1/14. The reading may be made in two ways:

(a) On a standard curve corresponding to a scale in water

Figure 2:
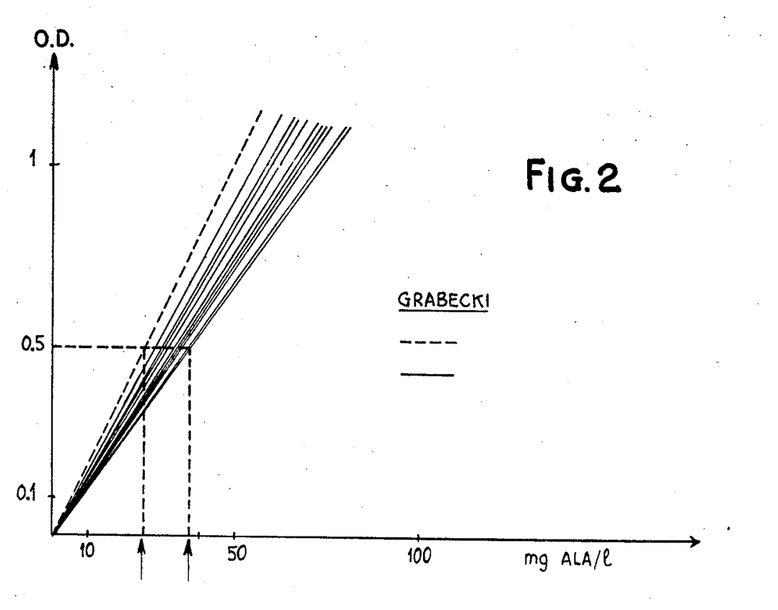
FIG. 2 is a graph of ALA scales produced from the results of measurement on ten urine samples using Grabecki's technique.

FIG. 2 of the accompanying drawings shows the dispersion obtained against the urines. The uncertainty in respect of determination is systematic and by default. It may be as much as −65%. The technique studied has a final dilution of 1/20.

(b) By means of an internal standard

In this case, the reading is carried out on a curve prepared from the urine under analysis. There is no longer any dispersion due to the urines. Random uncertainty of determination persists, however, and may be as much as ±5%. In respect of the determination of ALA, only one technique gives satisfactory results which is that derived from the Grabecki method, using an internal standard. However, this technique is applied directly to the urine and not to an eluate of urinary metabolites. The present Applicants have therefore adapted this technique to the specific case of the determination of ALA desorbed from an activated resin and in their method the optical density of the coloured complex produced by Ehrlich's reaction and rectified by comparison with the optical density of a blank which has received only Ehrlich's reagent and which has not received acetyl acetone is read on a calibration curve for ALA in water and determined by means of the activated resin.

The correction carried out on the basis of the optical density of the blank makes it possible to allow for the reactions of Ehrlich's reagent with compounds other than pyrrole formed from ALA and which are not eliminated on washing.

Also, the use of a standard scale prepared in water and determined by means of the activated resin eliminates the risk of error due to the latter. The accuracy of determination is ±5%.

In another aspect of the present invention, the suitably activated material comprised by the paper is a silica gel.

A paper of this kind may be used, for example, for determining trichloroacetic acid and trichloroethanol conjugated with glucuronic acid, such urinary metabolites being indicative of trichloroethylene poisoning.

The choice of this type of immobilizing paper for carrying out the above determination was made by subjecting various commercial immobilizing papers to fixing tests using trichloroacetic acid labelled with carbon 14.

The performances of the silica gel treated paper will be apparent from Table IV which indicates the following:

the nature of the solution for washing the strip of paper after immersion in the solution containing the labelled trichloroacetic acid, and drying;

the percentage loss of labelled trichloroacetic acid in each wash in comparison with the quantity retained;

the nature of the washing-out solution; and the percentage of trichloroacetic acid finally washed out by comparison with the quantity retained.

TABLE IV

| Wash solution | | Silica gel treated paper | |
|---|---|---|---|
| | | Benzene | Cyclohexane |
| Percentage of TCA Loss relatively to quantity retained | 1st wash | 2% | 0 |
| | 2nd wash | 1.7% | 0 |
| | 3rd wash | 1% | 0 |
| Washing-out solution | | Water or phosphate buffer | Phosphate buffer |
| Percentage of TCA washed out relatively to quantity retained | | 93% | 98% |
| TCA = trichloroacetic acid | | | |

It will be noted that washing is not carried out with water, but with a suitable non-polar solvent. Cyclohexane gives satisfactory results. Prior to use, the silica gel treated paper is activated by dehydration. The amounts of trichloroacetic acid and trichloroethanol in the eluate are determined by means of the method of Ogata et al.

In a first stage this method comprises hydrolyzing the conjugated trichloroethanol and then, in a second stage, reacting the trichloroacetic acid and the liberated trichloroethanol with pyridine in a hot alkaline medium. A reddish-orange colour develops. By means of calibration curves, the trichloroacetic acid and trichloroethanol concentrations can be read off from the colorimeter at two different wavelengths.

In the method of the present invention, urinary creatinine can be determined using paper treated with an ion-exchange resin or silica gel.

It is well known that the determination of creatinine (the elimination of which is substantially constant throughout the day) may be used to determine the dilution of the urine sample and to rectify the results of other tests carried out on the urine sample depending on such dilution. More particularly, it is conventional to express the determination of ALA in terms of mg of ALA per g of creatinine (standardization of the result).

In the present method, this standardization technique also offers the advantage of eliminating any risks of error due to the use of an immobilizing paper as the sampling means and hence due to the absence of an exact measurement of the amount of the sample taken.

The method of the present invention has the advantage of enabling the or each required urinary metabolite (e.g. ALA or conjugated trichloroethanol and trichloroacetic acid) and the urinary creatinine to be sampled in a single operation using the same immobilizing support.

The activated material on which the wanted urinary metabolites and the creatinine are both fixed, is washed, dried, and washed out, as described above. An aliquot part of the eluate is then used for determination of the or each wanted urinary metabolite whilst another aliquot part is used for determination of the creatinine. The result found for the or each wanted metabolite is then related to that found for the creatinine.

As for the determination of the ALA, a polystyrene skeleton resin having a functional group $ArSO_3H$ activated so as to be in the $H^+$ form, which is more satisfactory than the $NH_4^+$ and $Li^+$ forms, may be used for sampling and fixing the creatinine.

This will be apparent from Table V:

TABLE V

| Strips of paper impregnated with polystyrene —$ArSO_3H$ resin | Activated forms | | | Non-activated form |
|---|---|---|---|---|
| | $NH_4^+$ | $Li^+$ | $H^+$ | $Na^+$ |
| Quantity fixed: | 100% | 100% | 100% | 100% |
| Loss on 1st wash | 56.55 | 48.4 | 4.8 | 68.5% |
| Loss on 2nd wash | 16.5 | 15 | 3.8 | 16% |
| Recovered from the eluate | 26.8 | 36 | 91.4 | 15.4% |

It will be seen from this Table that the activated form $Li^+$ retains creatinine the compound better than the nonactivated $Na^+$ forms, although this is not the case with the ALA. The activated resin on which the creatinine is fixed is treated as hereinbefore described with reference to the ALA determination. The resin is washed several times with water, with agitation, dried, and then desorbed by bringing it into contact with an acid buffer solution.

The creatinine is determined by Jaffe's method in which the creatinine is reacted in a basic aqueous medium with a sodium picrate solution to form a coloured complex which is determined colorimetrically. In the specific case of the determination of creatinine washed out from a resin, the effect of the acid buffer used for the desorption of the creatinine must be neutralised prior to, or simultaneously with, the introduction of the reagents required for Jaffe's reaction. If this is not done, the amount of base to be added according to Jaffe's reaction will not be sufficient to bring the medium to a basic pH and the reaction will not take place.

As for the determination of ALA, the optical density of Jaffe's reaction product is corrected by allowing for the optical density of a blank in which the amount of eluate has been replaced by a corresponding amount of water, and the value found is read off from a calibration curve in respect of creatinine in water determined by means of the activated resin.

A silica gel treated paper may be used for sampling and fixing the creatinine. The creatinine is then washed out as described in connection with the determination of the trichloroacetic acid and trichloroethanol, and determined by Jaffe's method as described above.

The present invention also relates to apparatus for carrying out the method of the invention. This apparatus comprises:

a tube closed at one end and open at the other end;

a plug adapted to provide a sealing closure of the open end of the tube;

a paper strip treated with an appropriately activated substance and received in the tube; and means for securing the paper strip to the plug.

In a preferred embodiment, the tube comprises a stop member adapted to immobilize a body of a dehydrating product against the tube end, e.g. a silica gel pellet.

Advantageously, the plug is hollow and the strip-securing means is an elastic member received in the plug recess or cavity, such member being provided with a slot in the plane of the longitudinal axis of the tube, the slot substantially separating the member into two parts interconnected only by a bridge or web of material and being adapted to be opened to receive one end of the paper strip, and closed to immobilize the strip when the elastic member is introduced into the plug recess or cavity.

In order to increase the area of contact between the elastic member and the strip, the slot is preferably bounded by solid walls. These walls advantageously have projections which contribute to immobilizing the strip.

Two embodiments of the method of the present invention will now be described by way of specific example.

EXAMPLE 1

Early diagnosis of lead poisoning

Figures 3, 4:
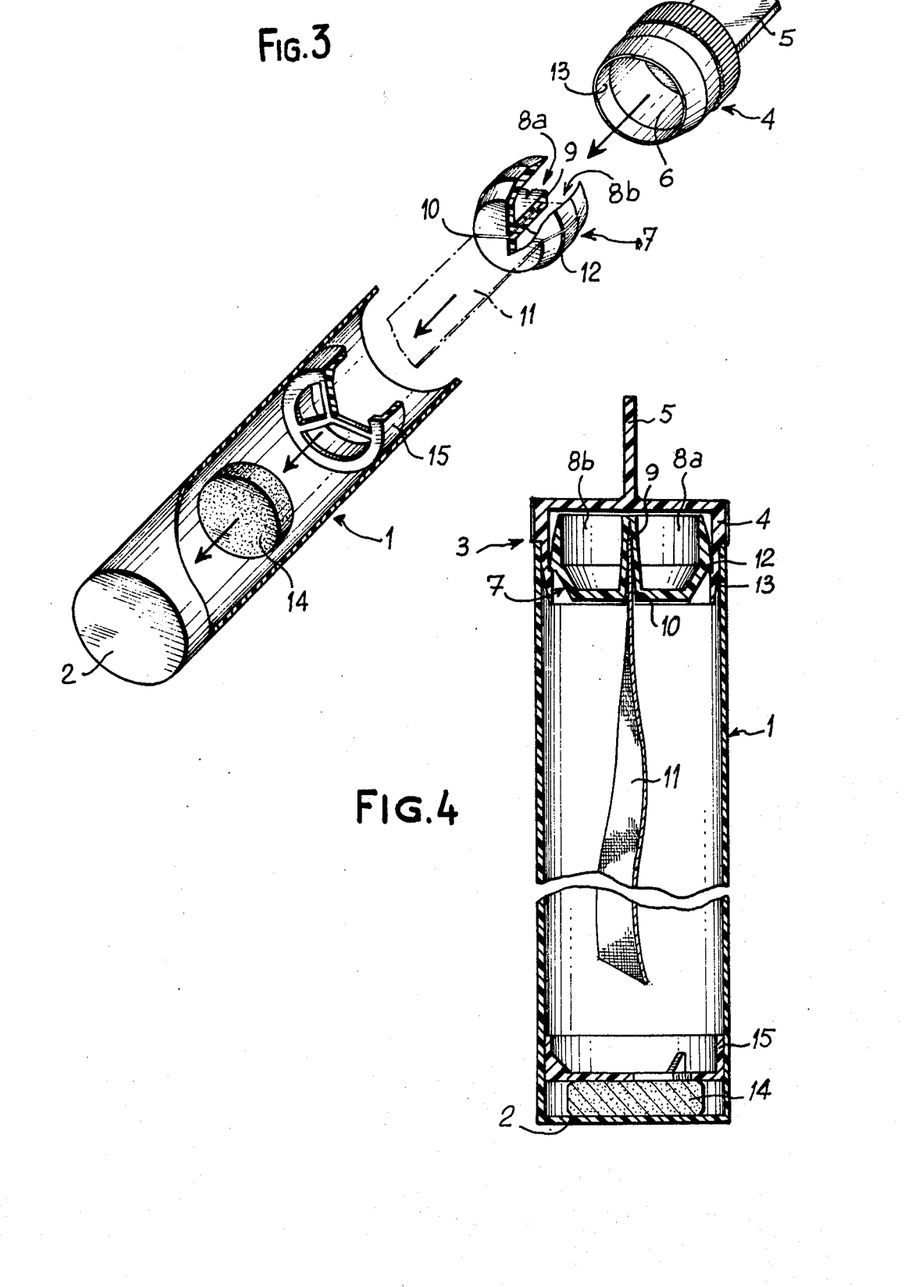
FIGS. 3 and 4 illustrate an apparatus for use in the method of the invention.

The invention is described in this Example with reference to FIGS. 3 and 4 of the accompanying drawing, which are respectively a perspective view in exploded form before assembly and a section after assembly of one embodiment of the apparatus of the present invention.

Referring to FIGS. 3 and 4, the apparatus comprises a tube 1, closed at one end by an end 2 and open at the other end 3. The open end 3 can be closed so as to be sealed by a hollow plug 4, provided with a gripper tap 5. An elastic member 7 subdivided into two compartments 8a and 8b fits into the cavity 6 of the plug 4. The two compartmebts 8a and 8b are connected only by a bridge of material 9 and together define a slot 10. Since the material of member 7 is elastic, the edges of the slot 10 can be moved apart and a strip of paper 11 inserted therein. Once the strip 11 is in position in the slot 10, the member 7 is inserted into the cavity 6 of the plug 4, where it is immobilized by its projecting periphery 12 bearing on a corresponding shoulder 13 provided on the inner surface of the plug 4. It will be seen that in this way the strip 11 is connected to the plug 4. The strip 11 consists, for example, of paper $SA_2$, i.e. paper impregnated with a polystyrene skeleton resin having activated $ArSO_3H$ functional groups.

To activate the resin, the strip impregnated with the non-activated resin is immersed for 15 minutes in a 2 N hydrochloric solution (bi-distilled water) which is periodically agitated. Bi-distilled water is then used for washing until the initial pH of the bi-distilled water is restored, and drying is carried out in atmosphere screened from light and basic fumes.

The strip 11 has a reference such as a mark (not shown) where it will be subsequently cut. The reference obviously enables the same strip length always to be cut so that the same amount of resin is always used. A dehydrating pellet 14 (formed, for example, by activated silica gel containing a coloured saturation indicator) is slid inside the tube.

This pellet is held in place by a stop member 15 which is force-fitted in the tube. Before use, the apparatus is in the form shown in FIG. 4. The apparatus is used as follows:

Sampling

The operator who receives the apparatus packed in opaque packing removes it therefrom and then removes plug 4 from tube 1 holding it by gripper tab 5. The strip of paper is then removed from the tube 1. The strip is immersed in the urine to be tested for about one second, wiped along the wall of the container containing the urine, and replaced in the tube by re-inserting the plug. During these operations it is advantageous to avoid exposure to bright light (direct sunlight, or a nearby fluorescent tube) and the presence of ammoniacal fumes in the surrounding atmosphere, since such fumes may affect fixation or the storage of the substances under analysis. The complete device is then placed in an envelope designed for this purpose and suitably identified, e.g. of the kind used for the dispatch of cine films to processing laboratories, and posted.

All of these operations are simple and fast to carry out and no skilled personnel is required. Consequently, this type of sampling is very suitable for mass examination, e.g. examination in a factory. After sampling, the strip is kept in the tube, where it finally dries by the dehydrating action of pellet 14. The strip can be left in this way for several days without harm, and this solves the problem of mass and intermittent arrival of samples at the laboratory.

Treatment at the laboratory

For analysis, the tube is opened, the strip is cut at the reference mark (the remainder being kept for control purposes, if necessary) and the cut portion of the strip is washed with distilled water by placing the piece of the strip in a dish containing 5 ml of bi-distilled water, the dish being positioned on a plate receiving a gentle and irregular movement. After immersion for 10 minutes the bi-distilled water in the dish is replaced by a fresh quantity of 5 ml of bi-distilled water and the immersion operation is repeated, with agitation, for 10 minutes. These prolonged and repeated washes eliminate most of the substances which are likely to interfere with subsequent analysis. The piece of strip is dried in the air and then immersed for 10 minutes, away from light, in 5 ml of 1 M acetate buffer pH 4.6. The metabolites fixed on the resin are desorbed and the eluate from this treatment is used for the determination of the ALA and creatinine.

ALA determination

Figure 5:
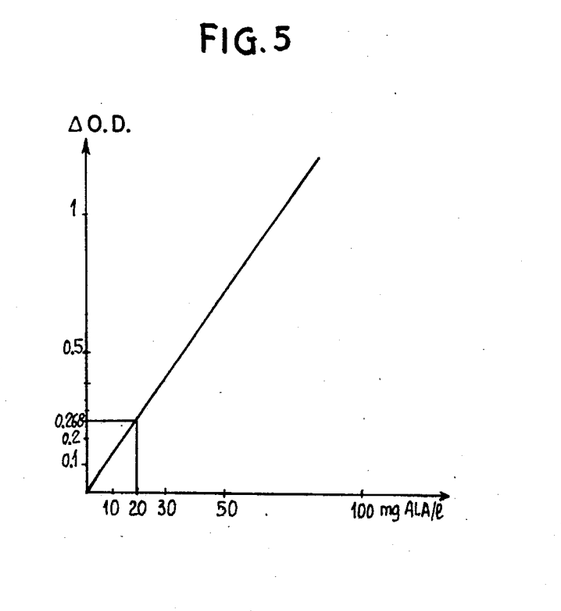
FIG. 5 is a calibration curve for ALA values obtained according to the method of the invention.

25 μl of acetyl acetone are introduced into a first tube and heated for 20 minutes on a water bath at 100° C. to form a pyrrole. The contents of the tube are allowed to return to ambient temperature whereafter 1 ml of Ehrlich's reagent is added to give a characteristic red colouring. The same operation is repeated in a second tube in which the amount of acetyl acetone is replaced by a corresponding amount of water. This tube acts as a blank for possible correction of the colouring given by Erlich's reagent with substances other than the pyrrole from the ALA. With a wavelength of $546.10^{-9}$m, the colorimeter is set to O on the blank (second tube), and then the optical density of the contents of the first tube is measured being, for example, 0.268. To allow for the risk of error due to the resin and the paper of the strip, a correction is carried out by reading the above result on a water calibration curve prepared as follows: a range of solutions of ALA in water is prepared with increasing concentrations (from 2 mg by 2 mg steps per 100 ml) and sampling is carried out by means of strips as if urine were involved. The strips then receive the same treatments as indicated above, i.e. washing, desorption, Ehrlich's reaction and measurement of the optical density for each ALA concentration relative to a blank. The values found enable the curve shown in FIG. 5 to be plotted. The optical density found for the sample, i.e. 0.268, corresponds to an ALA content of 20 mg ALA/l according to the water calibration curve.

Determination of creatinine

Figure 6:
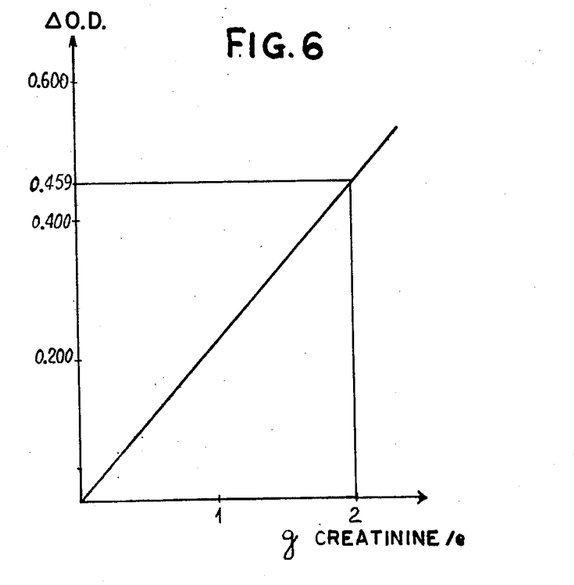
FIG. 6 is a calibration curve for creatinine values obtained according to the method of the invention.

Three drops of 20% NaOH (20 g/100 ml) and 1 ml of eluate are introduced into a first Eppendorf tube and agitated for 30 seconds to neutralize the acetate buffer used for the desorption. 200 μl of saturated picrate acid and then 100 μl of 7% NaOH are sampled. Agitation is carried out for 30 seconds to obtain thorough mixing and the mixture is left for 20 minutes in darkness during which time an orange colour forms. A blank is prepared in a second Eppendorf tube using the above procedure but replacing the 200 μl of eluate with 200 μl of distilled water. With a wavelength of 546 nm the colorimeter is set to 0 on the blank (second tube) and then the optical density of the contents of the first tube is measured being, for example, 0.459. As in the case of the ALA determination, to allow for the risk of error due to the resin and the paper of the strip, a correction is carried out by reading the above result off from a water calibration curve prepared in the same way as the ALA calibration curve, and which is shown in FIG. 6. The optical denstiy measured above corresponds to a creatinine content of 2 g/l. Comparison of the results (20 mg ALA/l and 2 g creatinine/l) shows that the urine of the subject contains 10 mg ALA/g of creatinine.

EXAMPLE 2

Early diagnosis of trichloroethylene poisoning

In this case, a silica gel treated paper was used packed in the same way as the ion-exchange resin treated paper described in Example 1. Activation of the silica gel was effected by a dehydrating pellet 14 provided to dry the strip of paper after immersion in the urine and draining.

The urine is sampled in the same way as the sampling carried out for the determination of ALA.

Treatment in the laboratory

After opening the tube in which the strip is replaced after sampling, the strip is cut at the reference mark and the cut part washed.

The procedure of Example 1 is followed using cyclohexane instead of water. Unwanted metabolites are removed in this way and the strip of paper is dried in air and then immersed for 10 minutes in 5 ml of water or 0.2 M phosphate buffer (pH 6). This operation liberates the metabolites fixed by the silica.

The eluate obtained from the above treatment is used to determine the amounts of trichloroacetic acid, trichloroethanol and creatinine.

Determination of trichloroacetic acid and trichloroethanol

200 μl of eluate and 10 μl of β-glucuronidase (750 Fishman units) are introduced into a tube which is then heated at 37° C. for 40 minutes to hydrolyze the conjugated trichloroethanol, whereafter 200 μl of 50% NaOH and 1 ml of pyridine are added to the tube and heated at 95° C. for 5 minutes. A reddish-orange colour develops. After cooling, 800 μl of the pyridine layer is sampled and 200 μl of water added thereto. Two readings are taken with the colorimeter, one at $436.10^{-9}$m to measure the trichloroethanol concentration and the other at $546.10^{-9}$m to measure the trichloroacetic acid concentration and the results are obtained from calibration curves.

to prepare the calibration curves, a range of solutions is prepared which respectively contain 100, 300, 500 and 1000 mg/l of trichloroacetic acid and trichloroethanol (it would of course be more exact to start with conjugated trichloroethanol, but this compound is not available in this form and free trichloroethanol must therefore be used).

To plot the calibration curve for trichloroacetic acid, a sample is taken of each of the solutions of the range by using an identical strip to that used for sampling the urine and this strip is treated in the same way.

The trichloroethanol calibration curve is prepared similarly but by diluting beforehand solutions to 100, 300, 500 and 1000 mg/l and sampling the solutions using the same paper strip.

From these two calibration curves it is possible to determine that a urine sample treated by way of experiment and found to have an optical density of 0.280 at $436.10^{-9}$m, has a trichloroethanol concentration of 500 mg/l, and a sample found to have an optical density of 0.400 at $546.10^{-9}$m has a trichloroacetic acid concentration of 300 mg/l.

Determination of creatinine

The determination was carried out as in Example 1.

200 μl of eluate, 100 μl of 7% NaOH and 500 μl of saturated picric acid in water are introduced into a first tube, agitated for 30 seconds, and then left to stand for 20 minutes. An orange colour develops. A reactive blank is prepared in a second tube. The optical density is measured at $546.10^{-9}$m by setting the colorimeter to 0 for the blank.

With the same urine sample as used for determination of the trichloroacetic acid and trichloroethanol an optical density of 0.410 is found, and reference to a previously plotted calibration curve shows that this corresponds to a concentration of 2 g/l.

Standardization of results

Comparison of the results (500 mg/l of trichloroethanol and 300 mg/l of trichloroacetic acid/2 g/l of creatinine) shows that the urine of the subject contains 250 mg of trichloroethanol/g of creatinine and 150 g of trichloroacetic acid/g of creatinine.

From the foregoing description it will be appreciated that the method of the present invention enables a considerable number of samples to be processed under the most satisfactory conditions (storage, accuracy of result, cost-price etc.).

We claim:

1. In a method for sampling and fixing urinary metabolites on an immobilising support which is readily transportable to an analysis centre for determining at least one of the metabolites, which comprises the steps of:
   (i) contacting the support with the urine so as to sample a specimen thereof and to fix urinary metabolites on the support;
   (ii) transporting the support to an analysis centre;
   (iii) removing from the support unwanted metabolites which are likely to disturb the determination of the or each required metabolite; and
   (iv) eluting and determining the or each required metabolite, the improvement which comprises using as the support a paper comprising a substance selected from the group consisting of a chemically activated ion exchange resin and silica gel activated by dehydration and expressing the determination of the or each required metabolite in relation to the determination of a metabolite whose excretion is constant with time.

2. Method according to claim 1 wherein the support is in the form of a narrow paper strip which is dipped into the urine to be sampled.

3. Method according to claim 1 wherein the resin is selected from the group consisting of resins having a polystyrene skeleton and an $ArSO_3H$ functional group, resins having an aliphatic polymer skeleton and a —COOH functional group, resins having a polystyrene skeleton and a —$N(CH_3)_2$ functional group and resins having a copolymer skeleton and a polyamine functional group.

4. Method according to claim 1 wherein the resin is a resin having a polystyrene skeleton and an $ArSO_3H$ functional group, the resin being activated by being transferred from the $Na^+$ form to a form selected from the group consisting of the $NH_4^+$ form and $H^+$ form.

5. Method according to claim 1 wherein the resin is activated by being contacted with a compound which provides it with the required ion.

6. Method according to claim 1 for determining trichloroacetic acid and trichloroethanol conjugated with glucuronic acid wherein a urine sample is taken by means of a strip of paper containing silica gel, the strip is dried, washed in an appropriate non-polar solvent to remove unwanted metabolites, the washed strip is dried, washed out, the trichloroethanol conjugated by β-glucuronidase is hydrolyzed and the hydrolyzed eluate is reacted with pyridine in a hot alkaline medium to develop a reddish-orange colour which is measured colorimetrically at a wavelength of $546.10^{-9}$m to determine the trichloroacetic acid and at a wavelength of $436.10^{-9}$m to determine the trichloroethanol.

7. Method according to claim 1 for determining urinary trichloroacetic acid wherein a urine sample is taken by means of a strip of paper containing silica gel, the strip is dried, washed in an appropriate non-polar solvent to remove unwanted metabolites, the washed strip is dried and washed out and the eluate reacted with pyridine in a hot alkaline medium, to develop a reddish-orange colour which is measured colorimetrically at an appropriate wavelength and compared with a calibration curve.

8. Method according to claim 7 wherein the measurement is made at a wavelength of $546.10^{-9}$m.

9. Method according to claim 1 for determining urinary trichloroethanol conjugated with glucuronic acid wherein a urine sample is taken by means of a silica-gel treated paper strip, the strip is dried, washed in an appropriate non-polar solvent to remove unwanted metabolites, the washed strip is dried and washed out, the trichloroethanol conjugated by β-glucoronidase is hydrolyzed and the hydrolyzed eluate reacted with pyridine in a hot alkaline medium, to develop a colour which is measured colorimetrically at an appropriate wavelength and compared with a calibration curve.

10. Method according to claim 9 wherein the measurement is made at a wavelength of $436.10^{-9}$m.

11. Method according to claim 1 for determining creatinine wherein a urine sample is taken by means of a strip of paper containing silica gel, the strip is dried, washed in an appropriate non-polar solvent to remove unwanted metabolites, the washed strip is dried and washed out and the eluate is reacted in a basic aqueous medium with a sodium picrate solution, to develop an orange colouring which is measured colorimetrically at an appropriate wavelength and compared with a calibration curve.

12. Method according to claim 11 wherein the measurement is made at a wavelength of $546.10^{-9}$m.

13. Method according to claim 1 for determining deltaaminolevulinic acid (ALA) wherein a urine sample is taken by means of a paper strip containing a polystyrene skeleton resin having an $ArSO_3H$ functional group activated in the $H^+$ form, the strip is dried, washed to remove unwanted metabolites, and washed strip is dried and washed out, and the ALA is condensed with acetyl acetone to form a pyrrole to which Ehrlich's reagent is added to form a stained complex which is determined colorimetrically.

14. Method according to claim 13 wherein the optical density of the pyrrole complex, rectified by comparison with the optical density of a blank which has received only the Ehrlich's reagent and which has not received acetyl acetone, is read on a calibration curve.

15. Method according to claim 13 wherein the colorimetric measurement is made at a wavelength of $546.10^{-9}$m.

16. Method according to claim 1 for determining creatinine wherein a urine sample is taken by means of a paper strip containing a polystyrene skeleton resin having an $ArSO_3H$ functional group activated in the $H^+$ form, the strip is dried, washed to remove unwanted metabolites, the washed strip is dried and washed out and the creatinine reacted in a basic aqueous medium with a sodium picrate solution to form a coloured compound which is determined colorimetrically.

17. Method according to claim 16 wherein the optical density of the coloured compound, rectified by comparison with the optical density of a blank for which the test sample containing the creatinine has been replaced by a corresponding quantity of water is read on a calibration curve.

18. Method according to claim 16 wherein the colorimetric measurement is made at a wavelength of $546.10^{-9}$m.

19. Method according to claim 1 wherein the result of the determination of the or each required metabolite is expressed relative to the urine creatinine level.

20. Method according to claim 19 wherein the ALA and the creatinine are determined on two fractions of the same eluate.

21. Method according to claim 19 wherein trichloroacetic acid and trichloroethanol, on the one hand, and creatinine, on the other hand, are determined on two fractions of the same eluate.

22. An apparatus for sampling and fixing urinary metabolites which comprises:
- a tube closed at one end and open at the other end;
- a plug adapted to provide a sealing closure of the said open end of said tube;
- a paper strip treated with a reactive substance and received in said tube;
- means for securing said paper strip to said plug; and said plug being hollow and said strip-securing means comprising an elastic member received in the plug recess or cavity, the said elastic member being provided with a slot in the plane of the longitudinal axis of the tube, the said slot substantially separating said elastic member into two parts interconnected only by a bridge or web of the elastic material, said slot being adapted to be opened to receive one end of the said paper strip and closed to immobilize the said paper strip when said elastic member is introduced into said plug recess or cavity.

23. Apparatus according to claim 22 wherein said tube includes a stop member adapted to immobilize a body of dehydrating product against the tube end.

24. Apparatus according to claim 22 wherein said plug has a gripping member.

25. Apparatus according to claim 22 wherein said slot is bounded by solid walls.

26. Apparatus according to claim 25 wherein said solid walls have projections.

* * * * *

UNITED STATES PATENT AND TRADEMARK OFFICE
CERTIFICATE OF CORRECTION

PATENT NO. : 4,159,193
DATED : June 26, 1979
INVENTOR(S) : Philippe Gauntley et al It is certified that error appears in the above—identified patent and that said Letters Patent is hereby corrected as shown below:

Col. 3, line 36 in Table II, change "$H^{30}$" to --$H^{+}$--;

Col. 3, line 37 in Table II, change "$Na^{30}$" to --$Na^{+}$--;

Col. 3, line 44, insert "even" after retain;

Col. 3, line 55 in Table III, insert "%" after 0.4;

Col. 6, line 52, change "forms" to --form--;

Col. 10, line 31, change "to" to --To--;

Col. 12, line 40, change "and" to --the--.

Signed and Sealed this

Fifteenth Day of July 1980

[SEAL]

Attest:

SIDNEY A. DIAMOND

Attesting Officer

Commissioner of Patents and Trademarks